US008658099B2

(12) United States Patent
Ying et al.

(10) Patent No.: US 8,658,099 B2
(45) Date of Patent: Feb. 25, 2014

(54) INTEGRATED APPARATUS FOR CONDUCTING AND MONITORING CHEMICAL REACTIONS

(75) Inventors: Jackie Y. Ying, Singapore (SG); Tseng-Ming Hsieh, Singapore (SG); Jeremy Ming Hock Loh, Singapore (SG); Chunyan Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 230 days.

(21) Appl. No.: 12/746,510

(22) PCT Filed: Nov. 6, 2008

(86) PCT No.: PCT/SG2008/000425
§ 371 (c)(1),
(2), (4) Date: Jun. 4, 2010

(87) PCT Pub. No.: WO2009/072987
PCT Pub. Date: Jun. 11, 2009

(65) Prior Publication Data
US 2010/0248245 A1    Sep. 30, 2010

Related U.S. Application Data

(60) Provisional application No. 60/996,817, filed on Dec. 6, 2007, provisional application No. 61/064,871, filed on Mar. 31, 2008.

(30) Foreign Application Priority Data

Jun. 23, 2008    (WO) ................ PCT/SG2008/000222

(51) Int. Cl.
*G05D 23/00*    (2006.01)
(52) U.S. Cl.
USPC ........................................ 422/109; 422/82.12

(58) Field of Classification Search
USPC ......................... 435/6.1, 6.12, 287.2; 422/500
See application file for complete search history.

(56) References Cited

U.S. PATENT DOCUMENTS 5,994,056 A    11/1999  Higuchi
6,025,114 A    2/2000   Popat et al.
(Continued)

FOREIGN PATENT DOCUMENTS

EP    0200362 A2    12/1986
EP    0487218 A1    5/1992
(Continued)

OTHER PUBLICATIONS

Lee et al., "Microchip-based one step DNA extraction and real-time PCR in one chamber for rapid pathogen identification", Lab Chip, 2006, vol. 6, pp. 886-895.
(Continued)

*Primary Examiner* — Natalia Levkovich
(74) *Attorney, Agent, or Firm* — Klarquist Sparkman, LLP

(57)    ABSTRACT

Apparatus for conducting and monitoring chemical reactions comprises a base and a thermal cycler mounted on the base. A plurality of heat-conducting receptacles are mounted on the thermal cycler and in heat-communication therewith. Each receptacle comprises an opaque body defining a bore having an open end, a first window, and a second window. A cartridge is removably mounted on the receptacles. The cartridge comprises a plurality of light-transmitting reaction vessels, and conduits connected to the reaction vessels for processing and transferring fluid. The reaction vessels are received in the bores of the receptacles through the open ends of the bores. A light emitter is mounted on the base for illuminating the reaction vessels through the first windows of the reaction vessels. A light detector is mounted on the base for selectively receiving and detecting light emitted from the reaction vessels through the second windows of the receptacles.

28 Claims, 6 Drawing Sheets

(56) References Cited

U.S. PATENT DOCUMENTS

| | | | |
|---|---|---|---|
| 6,068,751 A | 5/2000 | Neukermans | |
| 6,167,910 B1 | 1/2001 | Chow | |
| 6,168,948 B1 | 1/2001 | Anderson et al. | |
| 6,171,785 B1 | 1/2001 | Higuchi | |
| 6,374,684 B1 | 4/2002 | Dority | |
| 6,565,815 B1 * | 5/2003 | Chang et al. | 422/198 |
| 6,664,104 B2 | 12/2003 | Pourahmadi et al. | |
| 6,783,736 B1 | 8/2004 | Taylor et al. | |
| 6,814,934 B1 | 11/2004 | Higuchi | |
| 6,818,185 B1 | 11/2004 | Petersen et al. | |
| 7,256,035 B1 * | 8/2007 | Schnell et al. | 435/287.2 |
| 2002/0030044 A1 * | 3/2002 | Brown | 219/386 |
| 2004/0053403 A1 | 3/2004 | Jedrzejewski et al. | |
| 2005/0148091 A1 | 7/2005 | Kitaguchi et al. | |

FOREIGN PATENT DOCUMENTS

| | | |
|---|---|---|
| EP | 0512334 B1 | 9/1999 |
| EP | 1203959 A1 | 5/2002 |
| EP | 0872562 B1 | 9/2002 |
| EP | 1878496 A1 | 1/2008 |
| JP | 2004-101292 | 4/2004 |
| WO | 99/67646 | 12/1999 |
| WO | 01/11374 A2 | 2/2001 |
| WO | 2005/033712 A1 | 4/2005 |
| WO | 2006/085948 A2 | 8/2006 |

OTHER PUBLICATIONS

Yeung et al., "A DNA biochip for on-the-spot multiplexed pathogen identification", Neucleic Acids Research, 2006, vol. 34, p. e118.
Liu et al., "Fully integrated microfluidic biochips for DNA analysis", International Journal of Computational Engineering Science, 2003, vol. 4, p. 145-150.
International Search Report and Written Opinion, mailed Jan. 19, 2009, in related PCT patent application No. PCT/SG2008/000425.
International Preliminary Report on Patentability, mailed Jun. 17, 2010, in related PCT patent application No. PCT/SG2008/000425.
International Search Report and Written Opinion, mailed Sep. 19, 2008, in related PCT patent application No. PCT/SG2008/000222.
International Preliminary Report on Patentability, dated Oct. 5, 2010, in related PCT patent application No. PCT/SG2008/000222.
Chinese State Intellectual Property Office, Office Action, issued Jul. 26, 2011 in related Chinese Patent Application No. 200880125925.1.
Japanese Patent Office, Notice of Reasons for Rejection, issued May 16, 2012 in related Japanese Patent Application No. 2010-536893.

* cited by examiner

INTEGRATED APPARATUS FOR CONDUCTING AND MONITORING CHEMICAL REACTIONS

CROSS-REFERENCE TO RELATED APPLICATIONS

This application claims the benefit of U.S. Provisional Application No. 60/996,817, filed Dec. 6, 2007 and U.S. Provisional Application No. 61/064,871, filed Mar. 31, 2008, the entire contents of each of which are incorporated herein by reference. The entire contents of PCT Application No. PCT/SG2008/000222, filed Jun. 23, 2008, also are incorporated herein by reference.

FIELD OF THE INVENTION

The present invention relates to an apparatus and method for conducting and monitoring chemical reactions, particularly nucleic acid amplification reactions.

BACKGROUND OF THE INVENTION

An integrated system for real-time polymerase chain reactions (PCR) is available from Cepheid under the brand name GeneXpert™. This system can automate sample preparation and perform steps for DNA extraction in a special cartridge that is coupled to the system. The cartridge includes a thin, diamond-shaped reaction vessel. The side walls of the reaction vessel provide optical windows for optically interrogating the content contained in the reaction vessel. The system includes optical excitation and detection assemblies and two opposing heating plates for heating the reaction vessel when the reaction vessel is received between the heating plates. A fan is provided in the system for cooling the heating plates. The system can perform heating and cooling cycles required for real time PCR and detect the presence of multiple target nucleic acids in the same cartridge.

SUMMARY OF THE INVENTION

It has been realized that conventional systems for conducting and monitoring chemical reactions can be improved and simplified. For example, the construction of the base system can be simplified. Further, it has been realized that an integrated apparatus may be provided wherein sample preparation, pre-treatment, reaction and detection can all be performed in situ. It is also desirable to provide an apparatus for conducting and monitoring chemical reactions with improved performance, relatively simple structure, relatively lower cost, or a combination of these features. In accordance with an aspect of the present invention, an apparatus for conducting and monitoring chemical reactions is provided. The apparatus comprises a base; a thermal cycler mounted on, the base; a plurality of heat-conducting receptacles mounted on the thermal cycler and in heat-communication therewith, each one of the receptacles comprising an opaque body defining, a bore having an open end, a first window, and a second window; a cartridge removably mounted on the receptacles, the cartridge comprising a plurality of light-transmitting reaction vessels, and comprising conduits connected to the reaction vessels for processing and transferring a fluid, the reaction vessels respectively received in the bores of the receptacles through the open ends of the bores; a light emitter mounted on the base for illuminating the reaction vessels through the first windows of the reaction vessels; and a light detector mounted on the base for selectively receiving and detecting light emitted from the reaction vessels through the second windows of the receptacles. The light detector may comprise a single photo-multiplier-tube (PMT). The apparatus may comprise a lens mounted on the base for focusing the light emitted from the reaction vessels onto the PMT. The apparatus may comprise a plurality of light emitters each positioned for guiding the light emitted from the light emitter toward a respective one of the first windows. A plurality of light emitters may be provided, each of which is positioned to illuminate a respective one of the reaction vessels. Each reaction vessel may have a generally cylindrical shape. The bores of the receptacles may be generally cylindrical. The first and second windows, of each receptacle may be configured to reduce transmission of light received from the second window to the light detector through the first window. The receptacles may consist of three receptacles. The light emitter may comprise a light emitting diode. The thermal cycler may comprise a cooler and a heater. The cooler may be a thermal electric cooler. The heater may be an electric heater. The cooler and heater may be integrated. The apparatus may comprise a heat sink mounted on the base, and the thermal cycler may be mounted on the heat sink. The apparatus may comprise a controller in communication with the thermal cycler for controlling the thermal cycler. The controller may be in communication with the light detector for receiving a signal in response to detection of light by the light detector. The controller may control the thermal cycler to selectively heat or cool the reaction vessels in response to receiving the signal. The apparatus may comprise a plurality of light filters each positioned between the light emitter and a respective one of the receptacles. The apparatus may comprise a light filter positioned between the receptacles and the light detector. The receptacles may be made of copper or brass. The conduits of the cartridge may comprise conduits configured for preparing and treating a sample to be reacted or detected and for transferring the sample to one or more of the reaction vessels. At least one of the reaction vessels of the cartridge may contain a reaction mixture. The reaction mixture may be a nucleic acid amplification reaction mixture. The reaction mixture may be a polymerase chain reaction mixture.

In accordance with another aspect of the present invention, there is provided a system comprising the apparatus described the preceding paragraph and a user interface in communication with the apparatus. The apparatus can generate an output, and the user interface can receive the output and displays information based on the output. The output may comprise output reflective of a light signal detected by the detector.

In accordance with another aspect of the present invention, there is provided a method of operating the apparatus described herein. In this method, a plurality of reaction mixtures are prepared in the cartridge and each reaction mixture is placed in a selected reaction vessel. The thermal cycler is controlled to selectively heat or cool the selected reaction vessels and thus the reaction mixtures in the selected reaction vessels. The reaction mixtures in different reaction vessels are sequentially illuminated with the light emitter(s). Light emitted from the reaction mixtures is detected with the light detector. The thermal cycler may be controlled in response to detection of the light emitted from the reaction mixtures. An output in response to a detection result may be displayed to a user.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

An integrated apparatus or system for conducting and monitoring chemical reactions is provided. The chemical reactions may be nucleic acid amplification reactions, including polymerase chain reactions (PCR) such as basic PCR or reverse transcriptase PCR (RT-PCR), or other reactions that require controlled heating/qooling and real time optical detection. For example, real time PCR can be conveniently conducted and monitored using such an apparatus or system.

Figure 1:
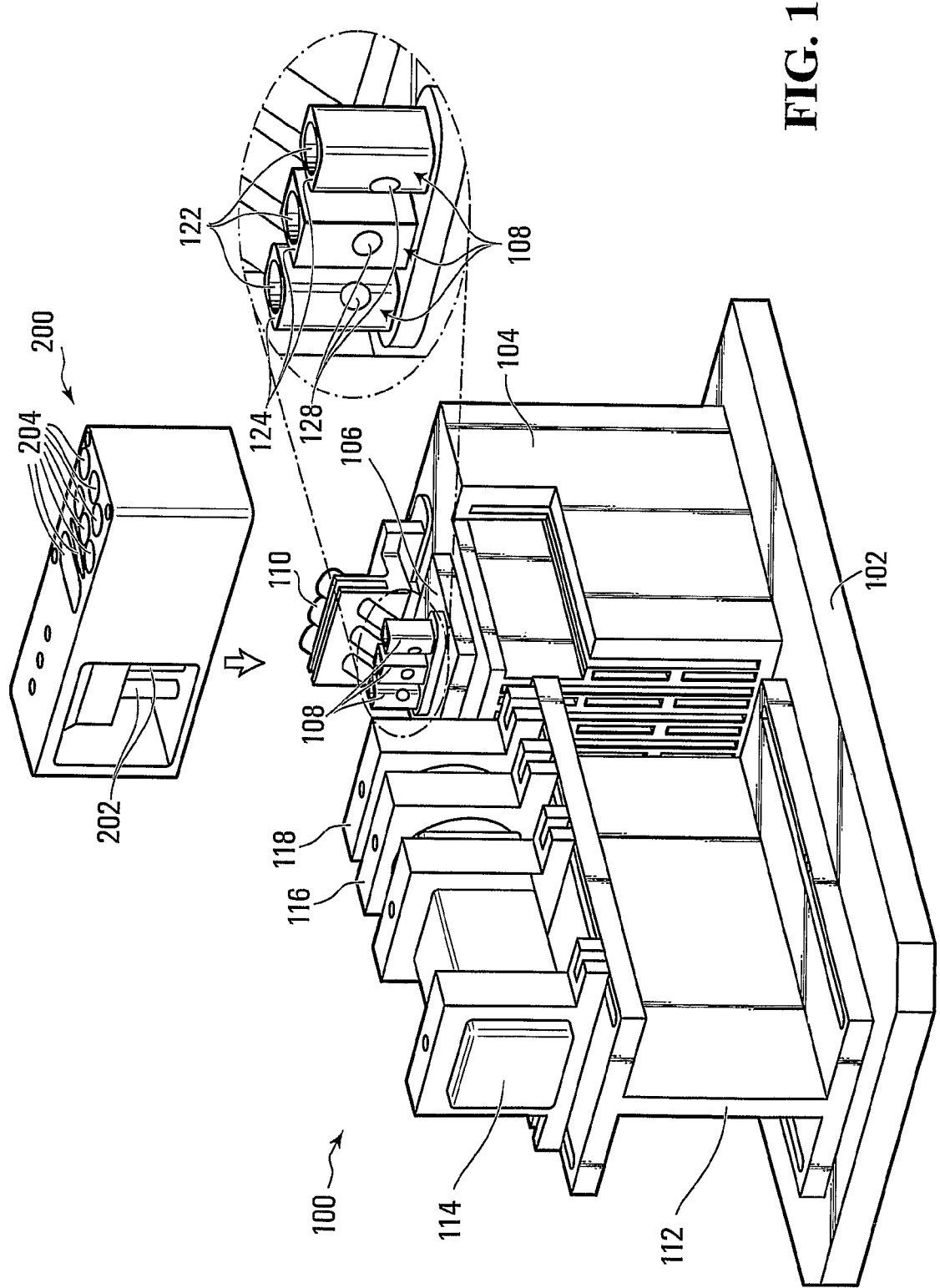
FIG. 1 is a perspective view of an apparatus for conducing and monitoring chemical reactions, exemplary of an embodiment of the present invention.
Figure 2:
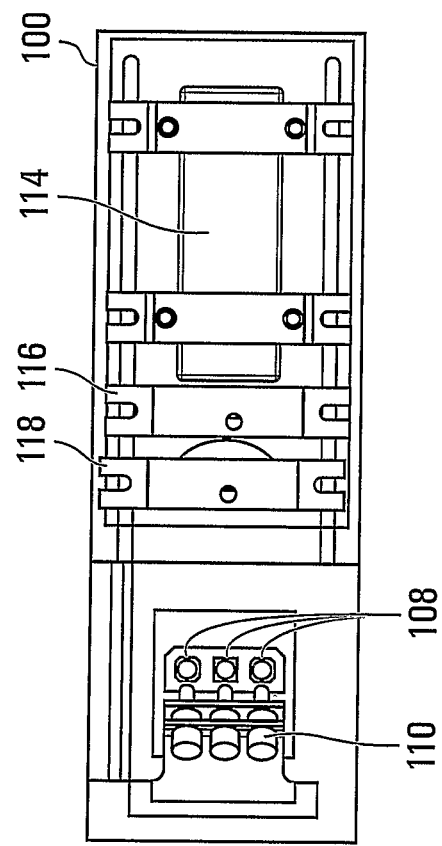
FIG. 2 is a top plan view of the apparatus of FIG. 1.
Figure 3:
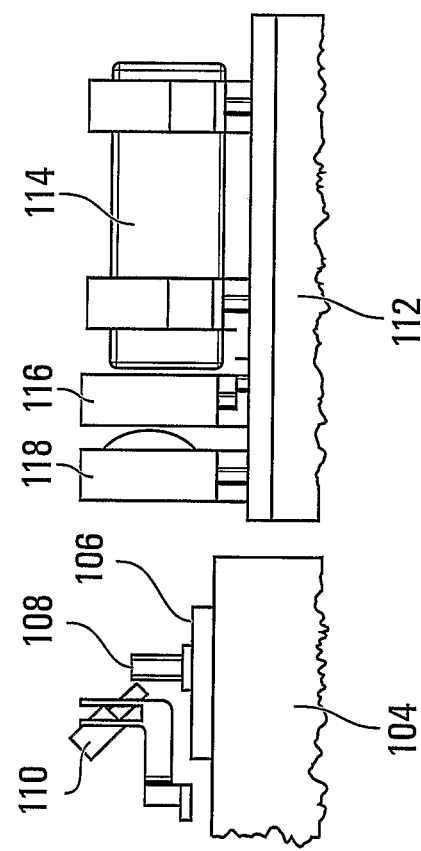
FIG. 3 is a side elevation view of the apparatus of FIG. 1.

FIG. 1 is a perspective, exploded view of an apparatus 100 for conducting and monitoring chemical reactions in a cartridge 200, exemplary of an embodiment of the present invention. Top and side views of apparatus 100, but without cartridge 200, are shown in FIGS. 2 and 3.

Apparatus 100 includes a base 102. A heat sink 104 is mounded on base 102. A thermal cycler 106 is mounted on heat sink 104: Heat sink 104 is thermally conducting for efficient heat exchange with thermal cycler 106. Heat sink 104 may be made of a suitable material and may have a suitable construction for effectively dissipating heat. For example, heat sink 104 may be provided with air-cooling features. Three heat-conducting receptacles 108 are mounted on thermal cycler 106. Three light emitters 110 are mounted on heat sink 104 adjacent receptacles 108. A support 112 is mounted on base 102 for supporting a light detector 114.

Detector 114 can be any suitable light detector or sensor for detecting and analyzing a light signal that is expected to be emitted from a reagent or a reaction product during use. For example, detector 114 may include a single photo-multiplier tube (PMT). Detector 114 is positioned and aligned to receive light emitted from different receptacles 108, as will be further described below. As can be appreciated, with a single detector, cost and complexity of the apparatus may be reduced.

A light filter 116 and an optical lens 118 maybe positioned in the optical path between receptacles 108 and detector 114 to focus and filter the light from receptacles 108. When used, lens 118 can conveniently focus lights from different receptacles 108 onto the same detector 114 for improved performance.

Figure 4:
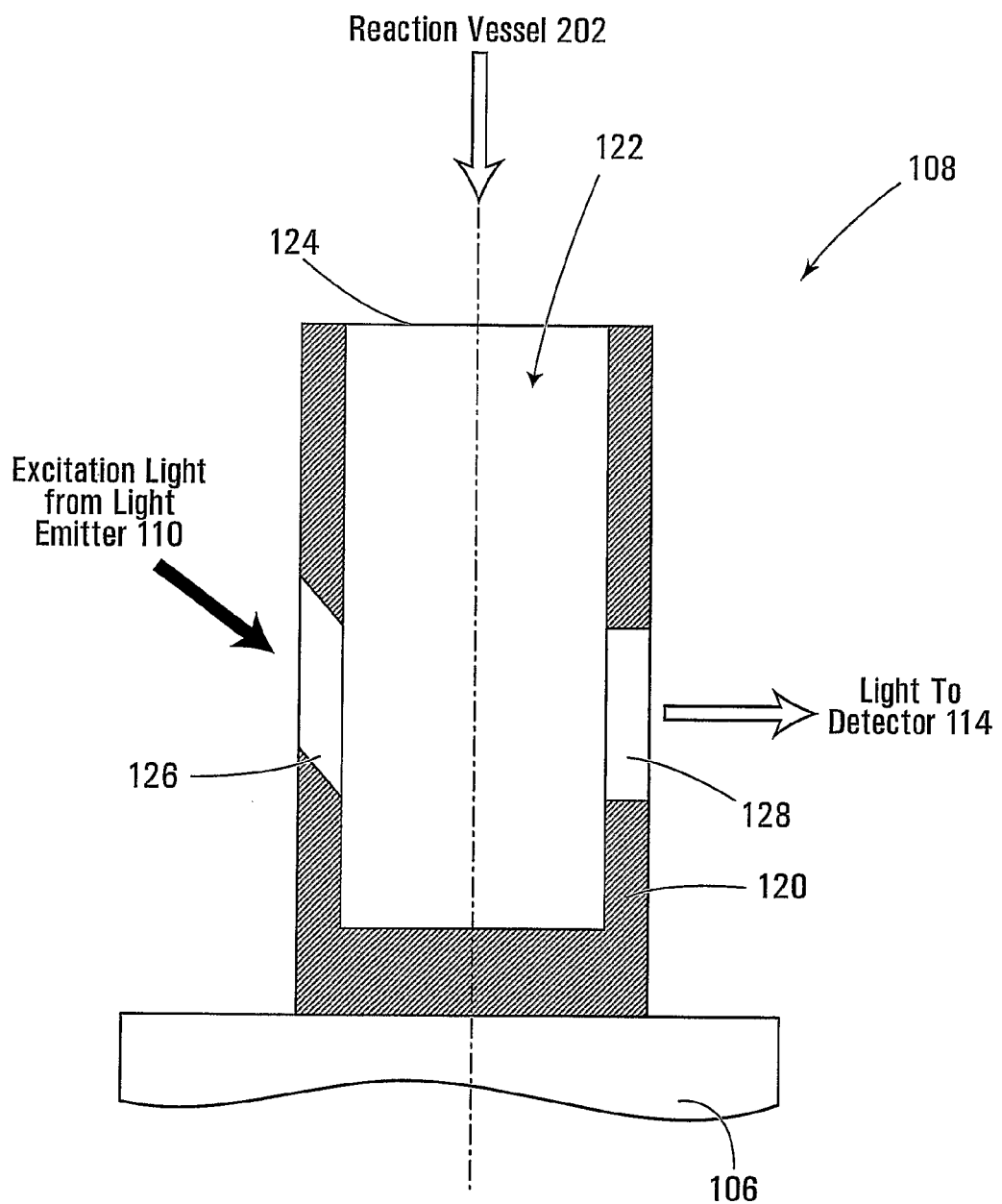
FIG. 4 is a cross-sectional view of a receptacle shown in FIG. 1.

As better shown in FIG. 4, each receptacle 108 has an opaque body 120. Body 120 may be formed from any suitable material that is sufficiently heat-conducting. For example, copper, brass, aluminum, or like materials may be used for forming body 120. Body 120 defines a bore 122 with an open end 124 for receiving a reaction vessel 202 of cartridge 202 (not shown in FIG. 4 but see FIG. 1). Bore 122 may be generally cylindrical. Bore 122 may also have a generally circular cross-section. The bottom end of bore 122 may be closed and may have a rounded or flat shape, or another shape.

On the side of receptacle 108 that is facing a corresponding light emitter 110, a first window 126 is provided for allowing light emitted from light emitter 110 to enter bore 122, and thus the reaction vessel 202 received in bore 112. On the side of receptacle 108 that is facing detector 114 (or lens 118 when it is provided), a second window 128 is provided for allowing detector 114 to receive and detect light emitted from the reaction vessel 202 received in bore 122. Windows 126 and 128 may have any shape. For example, they may be, generally circular or rectangular.

As depicted, bodies 120 may be separately formed and may each have a generally tubular shape. In other embodiments, bodies 120 of different receptacles 108 may be integrated into a unitary unit. For example, more than one receptacles may be formed in a unitary block with multiple bores.

In some embodiments, it may be desirable to reduce or prevent transmission of the incident excitation light received through window 126 (from light emitter 110) toward detector 114 through window 128. For example, as depicted in FIG. 4, the light emitter 110, windows 126, 128, and detector 114 may be configured so that the excitation light is directed at a downward angle, such as about 45 degrees, into window 126, while emission light received by detector 114 from window 128 travels in a generally horizontal direction. Such an arrangement can reduce light interference and the signal to noise ratio in the detected light.

As depicted in FIGS. 1 to 3 and 8, in the depicted embodiment three elongated receptacles 108 are positioned adjacent one another and are arranged in a generally parallel relationship. Each receptacle 108 extends upwardly with its opening end facing up. This arrangement may be convenient in some applications. For example, two or more generally parallel reaction vessels 202 may be provided in a corresponding cartridge, such as cartridge 200 shown in FIG. 1, so that multiple reaction vessels 202 can be conveniently simultaneously inserted into bores 122 of receptacles 108. Reactions in multiple reaction vessels 202 can be conveniently conducted and monitored simultaneously under substantially similar conditions.

Figure 8:
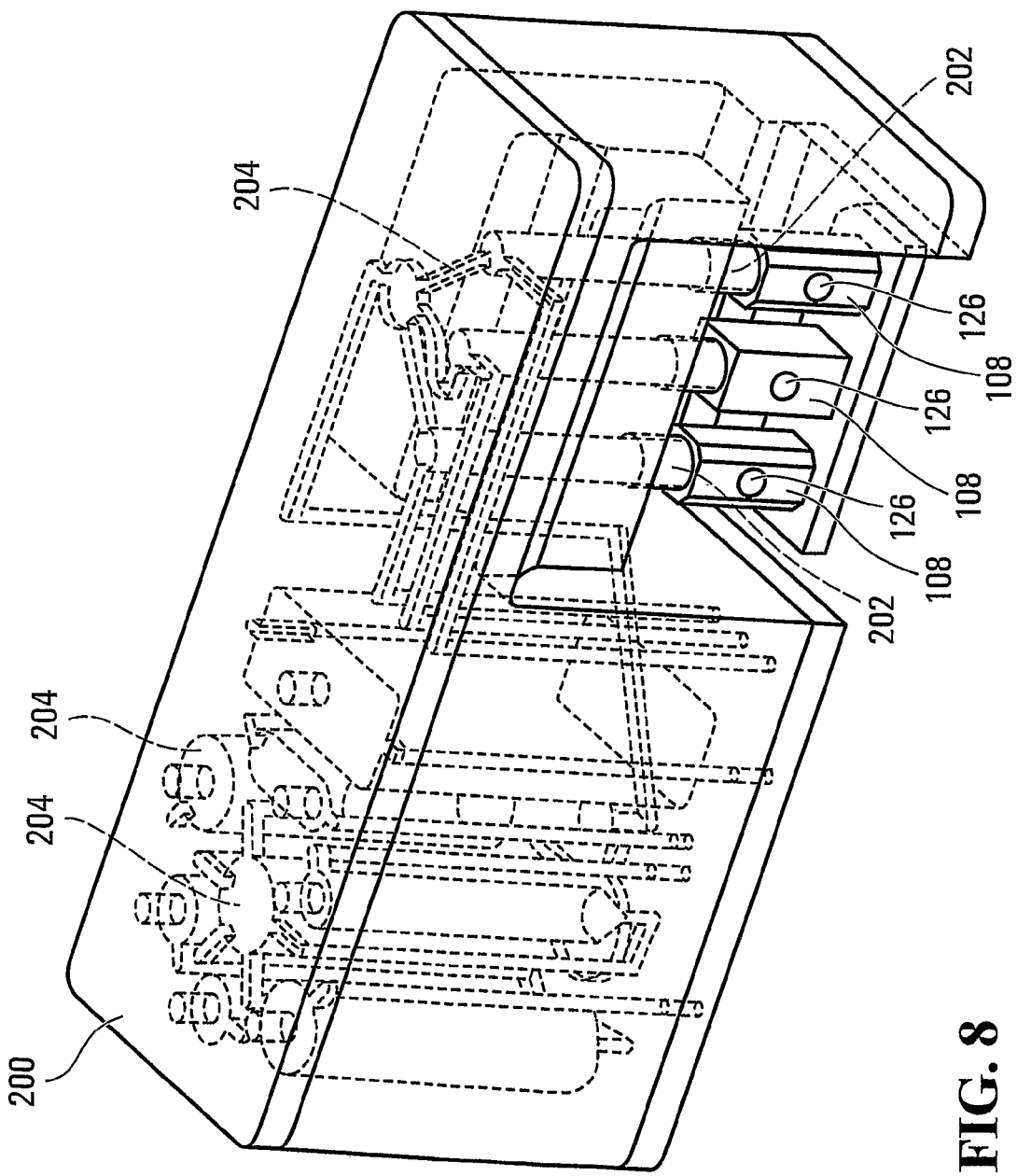
FIG. 8 is a rear see-through perspective view of the cartridge shown in FIG. 1.

During use, cartridge 200 is removably mounted on receptacles 108 (see FIG. 8). As depicted in FIGS. 1 and 8, cartridge 200 has several, e.g. three, light-transmitting reaction vessels 202 (only two are visible in FIG. 1)] and conduits 204 connected to reaction vessels 202 for processing reaction fluids and transferring fluids to and from reaction vessels 202.

As depicted, in the present embodiment cartridge 200 has three reaction vessels 202, which are respectively received in the three bores 122 of receptacles 108 through open ends 124. In other embodiments, more or fewer reaction vessels may be provided in a cartridge and it is not necessary that all of the reaction vessels are received in receptacles 108. It is also not necessary that each receptacle 108 receives one reaction vessel when the cartridge is mounted.

In some embodiments, cartridge 200 may be configured to provide integrated in situ sample treatment and processing. For this purpose, cartridge 200 may include various fluid chambers, connecting channels, and built-in fluidic devices for performing the processing tasks desired in a particular application.

In one embodiment, cartridge 200 may be configured to utilize pneumatic pressure for transferring a fluid between the different processing chambers in cartridge conduits 204.

For example, in an embodiment, the conduits of the cartridge (not shown) may include a plurality of pneumatic ports. Each port may be sealed with a seal and shaped to couple to a pneumatic conduit through the seal. The conduits may also include a plurality of chambers, each for receiving a liquid and having a first top opening and a first bottom opening. Each top opening is in fluid communication with a respective one of the pneumatic ports. The bottom openings are in fluid communication with one another through a connecting conduit provided above the bottom openings of the chambers. Therefore, selective application of pneumatic pressures to the chambers through the pneumatic conduits can transfer a liquid from one chamber to another chamber through the connecting conduit. The conduits of the cartridge may be constructed according to the disclosure of PCT application No. PCT/SG2008/000222, with modifications in view of the description herein.

Cartridge 200 may include any other desired fluidic transfer and flow control features.

Conveniently, cartridge 200 may be configured to process tissue samples, such as being provided with a tissue dissociation device for tissue sample preparation. Thus, tissue preparation, processing and PCR can be performed in the same cartridge while the cartridge is mounted on apparatus 100. The cartridge may also be pre-loaded with different agents such as a freeze-dried agent. The cartridge may, be designed to withstand a wide temperature range, such as from about 4° C. to about 100° C., or to a higher temperature that is desired for conducting the particular chemical reaction or for performing a processing step.

The walls of reaction, vessels 202 and the body of cartridge 200 around reaction vessels 202 may be made of a light-transmitting material so that light can be transmitted through the walls to and from the reaction solutions contained therein. A light-transmitting material may be transparent or translucent.

A light-transmitting reaction vessel 202 may be partially transparent or translucent. For example, windows may be provided for transmitting light therethrough. As can be understood, when windows are provided in reaction vessels 202, the windows should be positioned to match the locations of windows 126 and 128 in receptacles 108 respectively when cartridge 200 is mounted on receptacles 108.

In stead of providing a light-transmitting body around reaction vessels 202, cartridge 200 may be configured so that the space around reaction vessels 202 is clear of any light-blocking wall to allow the desired light transmission.

The walls of reaction vessels 202 should also be sufficiently heat-conducting so that the temperature of the reaction mixture contained in the reaction vessel is sufficiently responsive to the temperature change in receptacles 108.

Conveniently, three receptacles 108 are sufficient to simultaneously measure reactions in a vessel that contains a sample solution, a vessel that contains a positive control solution, and a vessel that contains a negative control solution. However, in a different embodiment, the number of receptacles 108 may be increased or decreased depending on the particular application and other considerations such as cost and flexibility.

Thermal cycler 106 is used to alternatively heat or cool receptacles 108, which in turn heat or cool the reaction vessels received in the bores 122 of receptacles 108 and the reaction mixtures or solutions contained therein. In some embodiments, thermal cycler 106 may include a separate heater (not separately shown) and a separate cooler (not separately shown). The heater may be any suitable heater. For example, an electric heater may be used. The cooler may be any suitable cooler. For example, a fan may be used as a cooler. In some embodiments, the heater and cooler may be integrated in thermal cycler 106. For example, a thermal electric cooler/heater, or Peltier heat pump, may be used in thermal cycler 106.

It should be understood that in different embodiments, it is not necessary that the spatial relationships between heat sink 104, thermal cycler 106 and receptacles 108 are as shown in the figures. It is sufficient that they are in a heat-exchange relationship or in good thermal contact with one another so that the temperature of receptacles 108 can be controlled by thermal cycler 106. It may be advantageous in some embodiments that heat sink 104, thermal cycler 106 and receptacles 108 are arranged to effectively and efficiently cycle the temperature of receptacles 108 through a selected temperature range with the desired cycling rate. In this regard, the arrangement depicted in FIG. 1 (and FIG. 3) may provide effective and efficient heat exchange between receptacles 108 and thermal cycler 106, for example when a thermal electric cooler/heater is used.

Each light emitter 110 may include a light source and a light guide (not separately shown) and may be configured and positioned to transmit and guide the emitted excitation light toward one of receptacles 108.

A light source may be separately provided or may be integrated with a light emitter 110. One or more light sources may be used light emitters 110 depending on the particular application. For example, different light sources may be used to emit lights that are of different spectra. Each light emitter 110 may include a light emitting diode (LED) as the light source. For different applications, the light sources may be adjusted, or substituted to provide different light intensity or spectrum or both. In some embodiments, each light emitter 110 may include a light filter (not separately shown in FIGS. 1 to 3 but see FIG. 5) positioned between the corresponding light source and receptacle 108 for filtering the light emitted from the light emitter in order to achieve a desired light spectrum, such as by blocking or absorbing light of undesired frequencies. For example, certain light frequencies may be filtered out to reduce interference with the emission light to be detected by detector 114.

Figure 5:
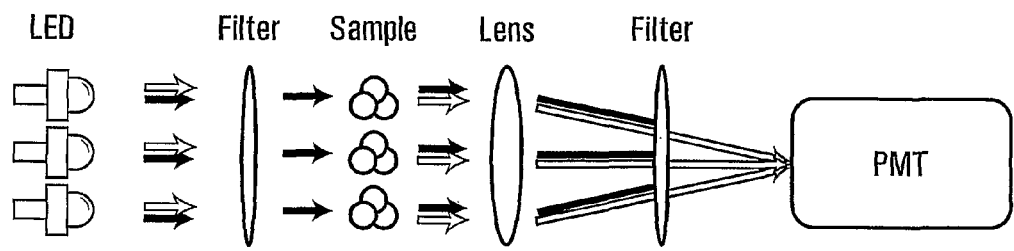
FIG. 5 is a schematic diagram of the optical components and light path in the apparatus of FIG. 1.

FIG. 5 schematically illustrates the inter-relationship of the optical components in an exemplary embodiment of present invention. In this embodiment, LEDs are used as light emitters. Excitation light emitted from the light emitters is transmitted to the samples through excitation filters. Light emitted by the samples are transmitted to a PMT through a focusing lens 118 and detection filter 116.

Figure 6:
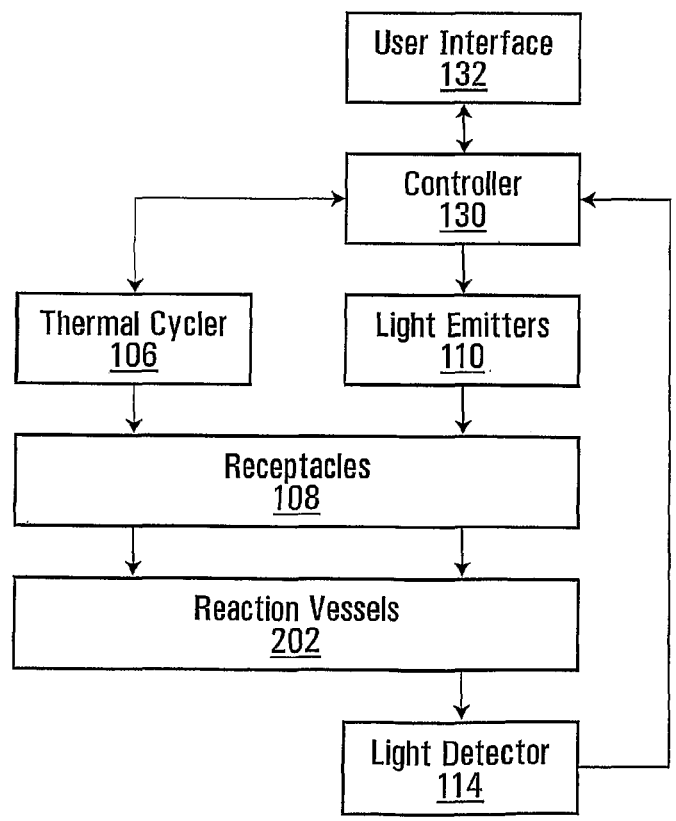
FIG. 6 is a block diagram illustrating a system for conducting and monitoring chemical reactions which includes the apparatus of FIG. 1, exemplary of an embodiment of the present invention.

As shown in FIG. 6, a controller 130 (not shown in FIGS. 1 to 3) may be provided for controlling the operation of apparatus 100. Controller 130 may be integrated with apparatus 100, such as mounted on base 102, or may be provided separately. In one embodiment, controller 130 is in communication with thermal cycler 106 for selectively heating or cooling receptacles 108. Controller 130 may also control the operation of light emitters 110 or their corresponding light emitter(s) to regulate the light received by the reaction vessels in bores 122. Controller 130 may also be in communication with detector 114 for receiving a signal in response to the detected light, and may control thermal cycler 106 to selectively heat or cool receptacles 108 in response to the received signal.

Controller 130 may be further in communication with a user interface . device 132 for receiving user input therefrom and for transmitting an output thereto. For example, the user input may include operation commands or operating parameters. The output may include data or results obtained during the chemical reactions. For instance, the detected light intensities may be displayed on user interface 132. User interface 132 may include any suitable computing interfacing device such as a computer. The computer for the user interface may be a portable computing device, such as a personal digital assistant (PDA) or the like. Controller 130 may have any suitable structure or hardware and software configuration. A controller typically used for controlling chemical reactions such as real time PCR may be used. Controller 130 may also include a general purpose or special purpose micro-controller. Some control functions may be provided either in controller 130 or in another component. For example, certain temperature control functions may be provided in controller 130, or may be provided in thermal cycler 106, or may be provided by an additional separate control unit such as a standalone thermal controller which is in communication with both controller 130 and thermal cycler 106. Some control functions may be provided either by hardware such as a circuit or by software such as a special or general purpose control program.

In some embodiments, controller 130 may include a central processing unit (CPU) or a computer that has a CPU. Controller 130 may be connected either by wire or wirelessly to communicate with various components such as thermal cycler 106 and detector 114, and other external devices (not shown).

Other peripherals for a controller or a computer, such as peripherals for input/output, communication, networking, data/signal conversion/transmission, signal amplification/filtering, may also be included, as can be understood by those skilled in the art.

For simplicity reasons, some components and features of apparatus 100 are not depicted in the FIGS. 1 to 6. A person skilled in the art can appreciate and understand that additional components and features may be added in order to perform certain functions. For example, a build-in or external power supply should be provided and connected to supply the power needed for proper operation during use. Various components may be secured together with screws, bolts and nuts, adhesive, or other fasteners. Wires may be used to electrically connect different electrical components. Sensors may be provided for measuring temperatures. Casing may be provided for enclosing a part or the entire apparatus.

In use, cartridge 200 is mounted on receptacles 108 by inserting reaction vessels 202 into respective bores 122 of receptacles 108. As can be appreciated, in some embodiments and applications, it is not necessary that each bore 122 receives a reaction vessel 202. One or more separate reaction vessels (not shown) such as separate test tubes may be inserted into one or more of bores 122. Further, a bore 122 may receive no reaction vessel in a particular application.

Each reaction vessel 202 may contain a selected reaction mixture. For example, with three receptacles 108, three reaction vessels 202 may be used, which may contain a sample solution, a positive control solution and a negative control solution respectively. The reaction mixtures may include reaction mixtures for a nucleic acid amplification reaction such as PCR. The nucleic acid may be ribonucleic acid (RNA) or deoxyribonucleic acid (DNA). For example, a sample mixture may include avian influenza virus RNA.

Reaction vessels 202 and the solutions contained therein are heated/cooled according to a pre-selected protocol for conducting the desired chemical reaction, such as PCR, by controlling the operation of thermal cycler 106 to selectively heat or cool receptacles 108. Receptacles 108 in turn heat or cool reaction vessels 202 and the reaction mixtures contained therein, depending on the temperature differences therebetween at any given time. The control of thermal cycler 106 may be provided by controller 130. The thermal cycling of thermal cycler 106 varies the temperature of receptacles 108, which due to their good heat-conducting property can effectively transfer heat to, or away from, the reaction vessels depending on the temperature differences therebetween. The desired temperature cycling profile can be readily determined by those skilled in the art.

For more precise temperature control, one or more temperature sensors such as thermal couples (not shown) may be provided, such as being imbedded in receptacles 108, for measuring the actual temperatures in receptacles 108. Temperature sensors may also be placed elsewhere such as in cartridge 200. The temperature sensors may be connected to thermal cycler 106 or controller 130 to provide feedback for temperature control.

When reaction vessels 202 are at the controlled temperature(s), excitation light with a selected spectrum and intensity may be transmitted sequentially to each reaction vessel 202 from the corresponding light emitter 110 through the corresponding window 126. For example, blue LEDs may be used to provide the source for the excitation light. The frequencies of the LEDs may be selected depending on the particular application and the desired excitation light frequencies. The spectra of excitation light for different reaction vessels may be different or the same depending on the application. The LEDs may be activated sequentially to emit pulsed light. For example, each pulse of light may have a pulse length of about 0.3 seconds.

As can be appreciated, light emitters 110 may be configured to direct the respective excitation light toward the corresponding windows 126 with reduced interference between different light emitters 100 or from background light. For the latter purpose, light emitter 110 may extend to close to the corresponding window 126. Further, a light filter, if desired, may be conveniently installed in light emitter 110 for improved performance.

When certain chemical, reactions occur in the reaction solutions, the reaction products may be fluorescent and can emit light of certain frequencies when they are excited by the excitation light received from light emitters 110. The light emitted by the solutions may be of a different spectrum than that of the incident light. The light emitted by the solution is transmitted through window 128 and is detected by detector 114. By detecting the intensity of light of selected frequencies, it can then be determined whether certain target substance is present in the reaction vessel. In this regard, lens 118 can help to guide and focus light emitted from windows 128 toward detector 114, thus increasing the detection sensitivity; and filter 116 can reduce the intensity of background or noise, thus improving signal to noise/background ratio.

To differentiate the signals from different reaction vessels 202, different reaction vessels 202 may be illuminated sequentially one at a time. The illumination period for each reaction vessel 202 may be relatively short, such as about 0.3 seconds, to allow faster cycle time. The illumination period however should be sufficiently long in order to obtain a detectable signal. Controller 130 may be used to control the activation of individual light emitters 110 and correlate the detected light signals with the respective reaction vessels 202 (thus the reaction mixtures therein).

As can be understood, in some applications, it is also possible to determine whether certain reactions have occurred by detecting and monitoring if the fluorescence emission from a fluorescent reagent has decreased. Such decrease may indicate that the amount of the reagent in the mixture has decreased due to certain chemical reactions.

The detected signal may be analyzed by controller 130 or output to another data analyzing device (not shown) for analysis. The detected signal and results may also be displayed on user interface 132. The detected signal from detector 114 may also be amplified or pre-treated by other signal processing techniques known to persons skilled in the art.

As can be appreciated, real-time control and monitoring of the chemical reactions in the reaction vessels can be conveniently achieved.

For a given application, controller 130 may be provided with special software components to execute commands and functions for, e.g., control of the system start-up, checking if any particular hardware is still functioning properly, control of thermal cycling for PCR operation, or optical detection of multiplex fluorescence signals in situ.

For instance, the apparatus may be programmed to detect light signals at the end of each annealing cycle during the thermal cycling of a PCR process.

Conveniently, a single detector may be used to detect emission lights from different reaction vessels 202, which receives excitation lights from different light emitters 110 (or LEDs).

The detected signals from detector 114 may be amplified and processed using a conventional signal processing computer program such as Labview™ program. The computer program may include functions for averaging the collected data. For example, the detected light signal may be converted to a electrical voltage signal, which varies with time. During each detection period for a reaction vessel (e.g. within 0.3 s), many, such as thousands, data points can be collected depending on the sampling rate. The computer program may provide a timed trigger to perform an averaging function to calculate the averaged signal strength within each (0.3 s) detection period. The trigger point may synchronized with the trigger for turning on the corresponding LED. The average of each particular detection period may be used as the data value for that particular period. The signal intensity can thus be plotted against the cycle number for each sample. The averaged data may then be displayed and continuously updated through the user interface, such as a PDA (personal digital assistant).

For performing PCR such as RT-PCR, the reaction vessels or chambers may be preloaded with PCR such as RT-PCR mixtures. The PCR mixtures may include primers and probes in lyophilized form. Light emitters 110 may be used to emit excitation light to stimulate fluorescence emission from the target product and detector 114 may be used to detect multiplex fluorescence signals emitted by the reaction solution in situ. The fluorescence signals may be quantitatively correlated with the original amount of RNA or DNA sample, such as using a computer or controller 230. Data may be automatically acquired, processed and displayed on user interface 232.

Conveniently, the receptacles have simple structures and are relatively inexpensive to construct, and can be used to receive various reaction vessels, including specially designed reaction cartridges and standard reaction vessels such as standard test tubes. In some embodiments, apparatus 100 may be configured for a particular application so that there will be no moving or rotating part when the apparatus is in use. This can provide improved reliability and relatively simple operation.

Another embodiment of the present invention is related to a system for conducting and monitoring chemical reactions, which includes apparatus 100 and a cartridge, such as cartridge 200, coupled to apparatus 100, as illustrated in FIG. 6. The cartridge has reaction vessels such as reaction vessels 202, which are simultaneously received in bores 122 of at least two receptacles 108 respectively. At least one of the reaction vessels contains a reaction mixture. The reaction vessels have transparent walls or windows for transmitting light therethrough. The system may also include a user interface such as a display unit that is in communication with apparatus 100 for receiving an output from apparatus 100 and displaying information based on the received output. The output of apparatus 100 may be reflective of a light signal detected by detector 114. The system may include a computer or microprocessor (not shown) for controlling its operation and managing its internal communication and communication with an external device.

Apparatus 100 may be modified. For example, it is not necessary that receptacles 108 are mounted directly on top of thermal cycler 106 and in direct contact with thermal cycler 106. It may be sufficient in some embodiments that receptacles 108 are mounted on thermal cycler 106 in a manner to allow thermal communication between them, such as through a heat-conducting intermediate.

The shapes and relative sizes of receptacles 108 may be varied depending on the particular application, and the structure of cartridge 200.

Windows 126 and 128 may be provided on adjacent sides, or on the same side, instead of on opposing sides. Each window 126 or 128 may be completely open or may be provided with a transparent panel such as a glass screen.

Base 102 may also be modified. For example, the various components of apparatus 100 may be mounted to a frame, which serves as the base. In another example, the base may include an adjustable support (not shown) for supporting a component, such as a lens, a filter, or a detector.

The distance between adjacent receptacles 108 may also be adjustable to allow use with different cartridges. Inserts (not shown) for bores 108 may be provided to allow use of difference reaction vessels that have different cross-sectional sizes or shapes.

The bodies 120 of receptacles 108 may have different wall thickness. The external shape of receptacles 108 may vary. As discussed above, in some embodiments, multiple bores 122 may be provided in a unitary block (not shown) of heat-conducting material for receiving multiple reaction vessels. The block may have any general shape. For example, it may have a generally rectangular shape.

In some embodiments, receptacles 108 may be enclosed in a closed environment, such as to reduce undesired change or fluctuation of environmental conditions or to reduce risks of contamination.

In some embodiments, cartridge 200 may be formed of three portions, a top portion, a middle portion, and a bottom portion. The three portions may be separate portions and the middle portion may be sandwiched between top and bottom portions. The top portion may be shaped as a flat plate with bolt holes. Alternatively, top portion may be formed of a thin film or sheet such as a plastic tape which has an adhesive side. For example, the adhesive side of the tape may have a glue layer on its surface. The bottom portion may be generally plate-shaped but provided with bolt holes, pneumatic ports sealed with breakable seals and fluid conduits or channels. Seals may be formed of an adhesive tape. Pneumatic ports may be sealed using the adhesive tape. Alternatively, bottom portion may also be formed of a flat sheet such as a plastic sheet with an adhesive side that faces middle portion. Each port may be shaped to couple to a pneumatic conduit, such as a needle, through the seal. The middle portion may define a number of chambers. Each chamber may have a top opening and a bottom opening. Each top opening may be connected with a pneumatic conduit or channel, which extends initially laterally and then downwardly to a respective pneumatic port in the bottom portion, so that the corresponding chamber is in communication with the respective port.

Each bottom opening may be connected with a liquid conduit or channel, which extends initially laterally and then upwardly towards a top connecting conduit that extends along the top surface of middle portion. The bottom openings may be connected to a well through the conduits or channels in the bottom portion. The well may be connected with a conduit or channel which extends upwardly to the connecting conduit. Thus, the chambers are each in fluid communication with a respective port through its top opening, and are in fluid communication with one another through their bottom openings and the connecting conduit.

When the three portions are affixed together such as with bolts and nuts or with an adhesive tape or thermo-diffusion bonding, the channels are tightly sealed and form closed fluid conduits for allowing fluid communication between the chambers and between the corresponding pairs of pneumatic ports and chambers. One of the chambers may be used as a gene extraction chamber, which is not necessarily connected directly to a pneumatic port.

A chamber in cartridge 200 may have a generally elongated cylindrical shape and a sloped bottom, and may extend vertically between the top and bottom portions. In different embodiments, the chambers 418 may have a different cross-sectional shape and may be longer or shorter.

Cartridge 200 may be formed using any suitable material. For example, each portion may be formed from a polymeric material, such as polycarbonate, poly(methyl methacrylate) (PMMA), or the like. The cartridge body may be formed using traditional machining techniques, such as microinjection molding and computerized numerically controlled (CNC) machining, or using plastic injection molding, as can be understood by persons skilled in the art.

The internal surfaces of the reaction vessels 202 and conduits 204 may be cleaned or sterilized when desired or needed. In some cases, the internal surfaces may be coated with another material to modify the surface properties.

The sizes or dimensions of cartridge 200 and the reaction vessels 202 and conduits 204 may vary depending on the application. For biological applications, the sample amount is typically small, thus reaction vessels 202 and conduits 204 may have dimensions on the order of micro-meters. When the dimensions are too large, it may be difficult to use pneumatic pressures to transfer small amounts of fluids. On the other hand, the dimensions should be large enough to allow sufficient transfer rate of the fluids under pneumatic pressures, and to allow sufficient light signals to be generated for detection. In some embodiments, fluid conduits 204 may have dimensions in the range of about 0.2 mm to about 1 mm. The reaction vessels and fluid chambers should have sufficient volumes for performing the particular desired reaction, process, or treatment. A conduit or chamber may have a volume on the order of 1 micro liter to 100 milliliter.

Different conduits or chambers may be provided in cartridge 200 for loading a sample, a lysis buffer, a conditioner, a wash buffer, and an elute buffer respectively. A gene extractor may be deposited in one of the conduits. The gene extractor may include a magnetic-based extractor, silica membrane, silica beads or another material that can attach to genes in a fluid with a high iron concentration. The genes may include DNA (Deoxyribonucleic acid), RNA (Ribonucleic acid), or mRNA (Messenger RNA). The gene extractor may be selected based on the particular genes to be extracted. Some of the conduits or chambers may be used for storing a reaction product, extracted genes, and a waste produced by the reactions respectively. DNA or RNA degradation reagent may also be preloaded in one or more chambers.

In some cases, adjustment of the gene binding condition may be required. The buffers loaded in the chambers may include buffers for gene binding (such as pure or 70% ethanol) based on the target gene binding conditions.

Gene extraction may be performed in cartridge 200 with a pre-treated sample fluid transferred from another chamber in the cartridge. Gene purification may be performed using a wash buffer stored in the cartridge. One wash buffer or different types of wash buffers may be used to wash the genes in multiple steps. If multiple wash buffers are used, two or more chambers may be allocated to store wash buffers. The waste may be later discharged if the cartridge is to be recycled, or disposed with the cartridge. Gene elution may also be performed in the cartridge. An elution buffer may be used to release the genes attached to the gene extractor and carries the genes to another conduit or chamber. The target genes may be collected to perform further reactions within cartridge 200. The extracted genes or other reaction products may be transferred to reaction vessels 202 for amplification or detection.

The modification discussed above is for illustration purposes and is not exhaustive. Other modifications are also possible.

EXAMPLE

A PCR mixture was prepared in a 0.2-ml PCR tube by mixing 15 µl of Taqman™ Fast Universal PCR Master Mix (#4352042, Applied Biosystems, Inc.), 1.5 µl of Taqman Assays-by-Design (Applied Biosystems, Inc.) containing primers and probe encoding for a green fluorescent protein (GFP) gene, 10.5 µl of deionized (DI) water, and 3 µl of cDNA converted from total RNA of brain tissue from transgenic GFAP-GFP mice by random hexamer priming using Taqman's reverse transcription (RT) reagent (190 N808-0234, Applied Biosystems, Inc.). The length of the amplicon was 82 bp.

25 µl of the PCR mixture was then transferred to a polycarbonate PCR chamber, followed by the addition of 15 µl of PCR oil to prevent evaporation.

The PCR chambers were mounted on a receptacle of a prototype of the apparatus as depicted in FIGS. 1 to 3. Three PCR chambers were mounted on the three parallel receptacles at the same time, which contained sample, positive control and negative control respectively.

PCR was performed by controlling the thermal cycler to obtain a temperature profile in the PCR chamber as follows: 95° C. for 20 s (activation of polymerase), 40 cycles of amplification (denaturation at 95° C. for 3 s, annealing and extension at 60° C. for 30 s).

Figure 7:
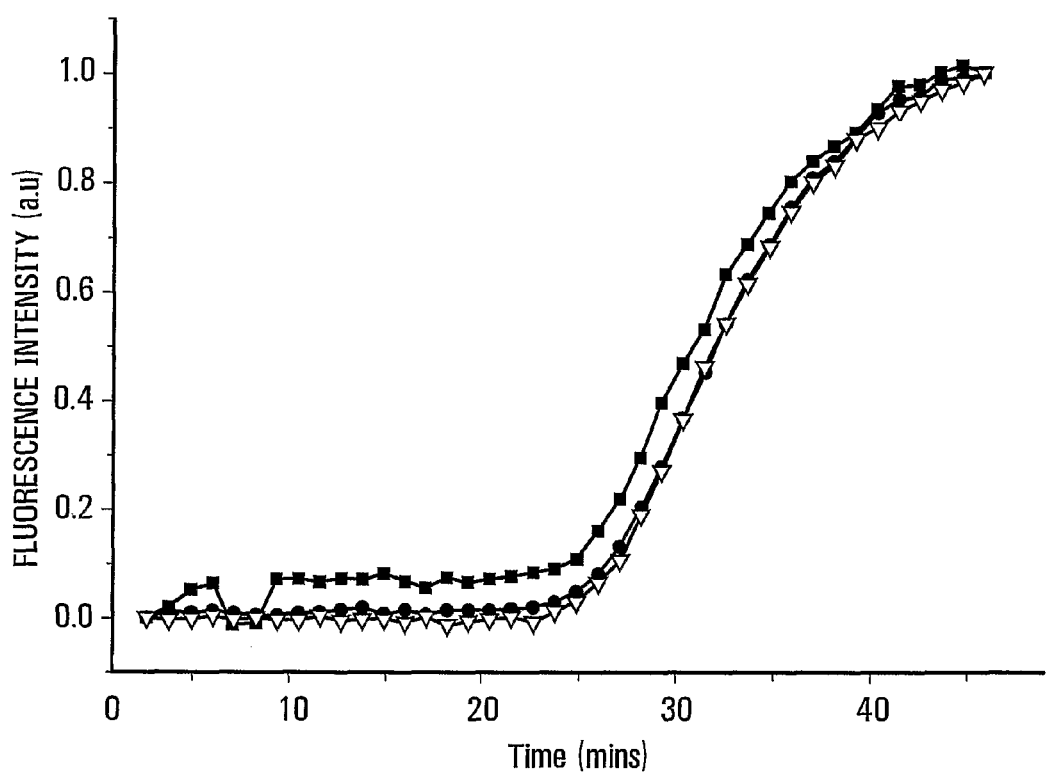
FIG. 7 is a line graph showing fluorescence intensity detected using the apparatus of FIG. 1.

Fluorescence arising from DNA replication was detected in real-time using the detector on the apparatus and recorded as a function of cycle number. The intensity of the detected fluorescence is shown in FIG. 7 as a function of time. The three data sets shown in FIG. 7 were obtained from the same sample in different sample volumes (15, 20 or 25 µl). The results indicate that the detected signal did not vary significantly with changes in sample volume. Some of the PCR products were separated and visualized in 2% agarose gel with ethidium bromide staining. The presence of a distinct band of 82 by was observed, which verified the real time detection result.

The test results confirmed that apparatus 100 can be used to automate PCR-based DNA testing and can be adapted to perform all necessary steps for conducting and monitoring PCR. With apparatus 100, it is possible to simultaneously perform tests on a sample along with a positive control and a negative control. Thus, more accurate testing results may be obtained.

An embodiment of the present invention may be conveniently integrated or adapted to couple with a sample preparation unit, such as a cartridge that uses pneumatic pressure to transfer fluids between internal fluid chambers. For example, the cartridge may be constructed according to PCT Application No. PCT/SG2008/000222, entitled "Fluid Processing and Transfer Using Inter-Connected Multi-Chamber Device" and filed Jun. 23, 2008, the entire contents of which are incorporated herein by reference.

Exemplary embodiments of the present invention may be used in a variety of fields and applications. For example, they may have applications in clinical and point-of-care disease diagnostics systems. They may also be used by emergency response teams, at airports or post offices, or other locations where prompt detection or testing is desired in order to prevent spreading of infectious diseases.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. An apparatus for conducting and monitoring chemical reactions, comprising:
a base,
a thermal cycler mounted on said base, said thermal cycler comprising at least one heater;
a plurality of heat-conducting receptacles mounted on said thermal cycler and in heat-communication therewith, each one of said receptacles comprising an opaque body defining a bore having an open end at an end of said body, a first window on a first side of said body, and a second window on a second side of said body;
a cartridge removably mounted on said receptacles, said cartridge comprising a plurality of light-transmitting reaction vessels, and comprising conduits connected to said reaction vessels for processing and transferring a fluid, said reaction vessels respectively received in the bores of said receptacles through the open ends of said bores;
a light emitter mounted on said base for illuminating said reaction vessels through the first windows of said receptacles;
a light detector mounted on said base for selectively receiving and detecting light emitted from said reaction vessels through the second windows of said receptacles; and
a controller electrically connected to said thermal cycler, said light emitter and said light detector,
wherein the first sides of said receptacles face said light emitter and said light emitter is configured and positioned to transmit light to said plurality of reaction vessels through the first windows on the first sides of said receptacles,
wherein the second sides of said receptacles face the light detector and said light detector is configured and positioned to receive and detect light emitted simultaneously from said plurality of reaction vessels,
wherein said controller is configured to control said thermal cycler to selectively heat or cool said reaction vessels to control temperatures therein, to control activation of said light emitter, and to receive and analyze a light signal from said light detector and correlate the light signal with a corresponding one of said reaction vessels.

2. The apparatus of claim 1, wherein said light detector comprises a single photo-multiplier-tube (PMT).

3. The apparatus of claim 2, further comprising a lens mounted on said base for focusing said light emitted from said reaction vessels onto said PMT.

4. The apparatus of claim 1, wherein said light emitter comprises a plurality of light emitters each positioned for guiding light emitted from a light source toward a respective one of said first windows.

5. The apparatus of claim 1, wherein said light emitter comprises a plurality of light emitters each positioned to illuminate a respective one of said reaction vessels.

6. The apparatus of claim 1, wherein said reaction vessels each has a generally cylindrical shape.

7. The apparatus of claim 1, wherein said bores of said receptacles are generally cylindrical.

8. The apparatus of claim 1, wherein said first window and said second window of said each receptacle are positioned, relative to said light emitter and said light detector, to reduce transmission of light from said light emitter to said light detector through said first window and said second window.

9. The apparatus of claim 1, wherein said plurality of receptacles consists of three receptacles.

10. The apparatus of claim 1, wherein said light emitter comprises a light emitting diode.

11. The apparatus of claim 1, wherein said thermal cycler further comprises a cooler.

12. The apparatus of claim 11, wherein said cooler is a thermal electric cooler.

13. The apparatus of claim 11, wherein said heater is an electric heater.

14. The apparatus of claim 11, wherein said cooler and heater are integrated.

15. The apparatus of claim 1, further comprising a heat sink mounted on said base, said thermal cycler being mounted on said heat sink.

16. The apparatus of claim 1, wherein said controller is configured to control said thermal cycler to selectively heat or cool said reaction vessels in response to receiving said light signal.

17. The apparatus of claim 1, further comprising a plurality of light filters each positioned between said light emitter and a respective one of said receptacles.

18. The apparatus of claim 1, further comprising a light filter positioned between said receptacles and said light detector.

19. The apparatus of claim 1, wherein said receptacles are made of copper or brass.

20. The apparatus of claim 1, wherein said conduits of said cartridge comprise a chamber for preparing and treating a sample to be reacted or detected and a conduit connecting said chamber to one or more of said reaction vessels for transferring said sample to said one or more of said reaction vessels.

21. The apparatus of claim 1, wherein at least one of said reaction vessels of said cartridge contains a reaction mixture.

22. The apparatus of claim 21, wherein said reaction mixture is a nucleic acid amplification reaction mixture.

23. The apparatus of claim 21, wherein said reaction mixture is a polymerase chain reaction mixture.

24. A system comprising the apparatus of claim 1 and a user interface device connected to said apparatus, wherein said apparatus is configured to generate an output, and said user interface device is configured to receive said output and display information based on said output.

25. The system of claim 24, wherein said output comprises output reflective of said light signal.

26. A method of operating the apparatus of claim 1, comprising:
   preparing a plurality of reaction mixtures in said cartridge;
   placing each one of said reaction mixtures in one of selected ones of said reaction vessels;
   controlling said thermal cycler to selectively heat or cool said selected reaction vessels and thus said reaction mixtures in said selected reaction vessels;
   sequentially illuminating said reaction mixtures in different reaction vessels with said light emitter; and
   detecting light emitted from said reaction mixtures with said light detector.

27. The method of claim 26, wherein said controlling comprises controlling said thermal cycler in response to detection of said light emitted from said reaction mixtures.

28. The method of claim 26, comprising displaying to a user an output in response to a result of said detecting.

* * * * *